US008927779B2

(12) United States Patent
Taillefer et al.

(10) Patent No.: US 8,927,779 B2
(45) Date of Patent: Jan. 6, 2015

(54) METHOD FOR THE HYDROXYLATION OF HALOGENATED ARYL COMPOUNDS

(75) Inventors: Marc Taillefer, Vailhauques (FR); Anis Tlili, Montpellier (FR); Florian Monnier, Montpellier (FR); Ning Xia, Illkirch-Grafferstaden (FR)

(73) Assignee: Centre National de la Recherche Scientifique, Paris (FR)

( * ) Notice: Subject to any disclaimer, the term of this patent is extended or adjusted under 35 U.S.C. 154(b) by 336 days.

(21) Appl. No.: 13/376,999

(22) PCT Filed: Jun. 8, 2010

(86) PCT No.: PCT/FR2010/051140
§ 371 (c)(1),
(2), (4) Date: Feb. 28, 2012

(87) PCT Pub. No.: WO2010/142913
PCT Pub. Date: Dec. 16, 2010

(65) Prior Publication Data
US 2012/0157704 A1    Jun. 21, 2012

(30) Foreign Application Priority Data
Jun. 8, 2009  (FR) ..................................... 09 02767

(51) Int. Cl.
C07C 37/02    (2006.01)
C07B 41/02    (2006.01)
C07C 41/26    (2006.01)
C07C 45/64    (2006.01)
C07C 253/30   (2006.01)
C07C 201/12   (2006.01)

(52) U.S. Cl.
CPC .................. C07C 37/02 (2013.01); C07B 41/02 (2013.01); C07C 41/26 (2013.01); C07C 45/64 (2013.01); C07C 253/30 (2013.01); C07C 201/12 (2013.01)
USPC ............ 568/797; 568/316; 568/650; 568/706

(58) Field of Classification Search
CPC ............................... C07C 37/02; C07C 39/07
USPC .................. 568/797, 706, 775, 774, 316, 650
See application file for complete search history.

(56) References Cited

PUBLICATIONS

Buck; Organic Letters, 2002, 4(9), 1623-1626.*
International Search Report for PCT/FR2010/051140, Jun. 10, 2010.
Kormos C M et al: "Direct conversion of aryl halides to phenols using high-temperature or near-critical water and microwave heating" Tetrahedron, Elsevier Science Publishers, Amsterdam, NL, vol. 62, No. 19, (May 8, 2006), pp. 4728-4732.
Zhao D. et al.: "Synthesis of phenol, aromatic ether, and benzofuran derivatives by copper-catalysed hydroxylation of aryl halides" Angewandte Chemie International Edition English, vol. 48, (Nov. 2, 2010), pp. 8729-8732.

* cited by examiner

*Primary Examiner* — Sudhakar Katakam
*Assistant Examiner* — Pancham Bakshi
(74) *Attorney, Agent, or Firm* — B. Aaron Schulman, Esq.; Stites & Harbison, PLLC.

(57) ABSTRACT

The present invention relates to a method for the hydroxylation of halogen aryl compounds carried out at a temperature lower than 200° C. in the presence of a catalytic system including a copper-based catalyst and a ligand L according to reaction scheme Formula (A), in which: R is selected from the groups having an acceptor inductive effect and the groups having a donor mesomer effect; M is selected from alkaline or alkaline-earth cations; X is a halogen atom; r is between 0 and 5; and the ligand L is selected from compounds having formula I.

23 Claims, No Drawings

METHOD FOR THE HYDROXYLATION OF HALOGENATED ARYL COMPOUNDS

The invention relates to a method for the hydroxylation of halogenated aryl compounds in the presence of a ligand. It particularly concerns a method for hydroxylating iodinated or brominated aryl compounds in the presence of a ligand to obtain phenols or diaryl ethers.

Phenols are used in numerous fields of application such as human, animal or plant health, materials or non-linear optics.

Hydroxylation reactions of halogenated aryl compounds are known to be one of the pathways for the synthesis of phenols.

The document <<Practical Imidazole-Based Phosphine Ligands for Selective Palladium-Catalyzed Hydroxylation of Aryl Halides>>, Beller et al, Angewandte Chemie International Edition, 2009, 48, 918-921, discloses hydroxylation reactions of halogenated aryl compounds in the presence of a palladium catalyst and modified imidazole-based phosphine complex ligands.

The document <<The Selective Reaction of Aryl Halides with KOH: Synthesis of Phenols, Aromatic Ethers and Benzofurans>>, Buchwald et Al, Journal of The American Chemical Society, 2006, 128, 10694-10695, also discloses a hydroxylation reaction of halogenated aryls in the presence of a palladium catalyst and a diaryl-based complex ligand.

These catalytic systems are toxic on account of the presence of palladium and are costly to implement. The document <<Direct conversion of aryl halides to phenols using high-temperature or near-critical water and microwave heating>>, C. M Kormos and N. E Leadbeater, Tetrahedron, 2006, 62, 4728-4732 discloses the use of a catalytic system combining copper iodide with L-Proline in a hydroxylation reaction of iodinated or brominated aryl compounds in an aqueous medium.

However, the reaction described in this document requires high temperatures, higher than 200° C., these temperatures being reached with a microwave heating system; in addition the yields obtained for the synthesis of phenols remain relatively low.

It is therefore a first objective of the present invention to propose a method for the hydroxylation of halogenated aryl compounds which overcomes the above-mentioned known disadvantages of the prior art.

Another objective of the present invention is to propose an economic method that can be given easy industrialization and is little toxic allowing the hydroxylation of halogenated aryl compounds under gentle conditions.

A further objective of the invention is to propose a method for the hydroxylation of halogenated aryl compounds with high yields.

As further objective, the present invention sets out to propose a method for the hydroxylation of halogenated aryl compounds that is easy to implement, has easy industrial applicability and is adaptable to a large variety of substrates, without any major change to operating conditions.

The subject of the present invention is a method for the hydroxylation of halogenated aryl compounds, implemented at a temperature lower than 200° C., in the presence of a catalytic system comprising a copper-based catalyst and a ligand L according to the following scheme:

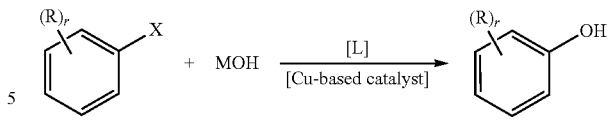

R being selected from the groups having an acceptor inductive effect and groups having a donor mesomer effect;
M being selected in the group consisting of alkaline or alkaline-earth cations;
X being a halogen atom;
r being between 0 and 5;
L is a compound of formula I

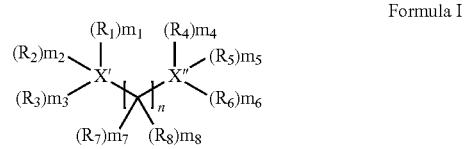

Formula I wherein
X', X", the same or different are selected in the group consisting of the nitrogen atom, the C=O group, the C=S group and the C—OH group;
$m_1$ to $m_8$, the same or different, represent 0 or 1;
n represents 1 or 2;
$R_1, R_2, R_3, R_4, R_5, R_6, R_7$ and $R_8$, the same or different, are selected in the group consisting of:
  a hydrogen atom;
  a branched, linear, monocyclic or polycyclic hydrocarbon group comprising 1 to 20 carbon atoms and possibly comprising one or more unsaturations in the form of double and/or triple bond(s), preferably methyl, isobutyl, phenyl;
  a primary, secondary or tertiary —NR'R" amine, wherein R' and R" the same or different represent a $C_1$ to $C_{10}$, alkyl group, preferably $C_1$ to $C_6$, linear or branched, preferably methyl;
  a hydroxyl group;
  or $R_4, R_5, X"$ and $R_7$ form a heterocyclic group, preferably pyrrolidine;
  or $R_1$, X' and $R_7$ form a phenol group;
  or $R_1, X', X", R_7$ and $R_4$ form a polycyclic group formed of at least 3 saturated and/or unsaturated rings, or of at least 3 rings of which only one or two thereof is (are) aromatic and forming between them ortho- or ortho- and peri-condensed systems, preferably the phenanthroline group.

In one particular embodiment, the ligand L is selected in the group consisting of the compounds of formula I wherein:
X', X", the same or different, are selected in the group consisting of the nitrogen atom, the C=O group, the C=S group and the C—OH group;
$m_1$ to $m_8$, the same or different, represent 0 or 1;
n represents 1 or 2;
$R_1, R_2, R_3, R_4, R_5, R_6, R_7$ and $R_8$, the same or different, are selected in the group consisting of:
  a hydrogen atom;
  a branched, linear, monocyclic or polycyclic hydrocarbon group comprising 1 to 20 carbon atoms and possibly comprising one or more unsaturations in the form of double and/or triple bond(s), preferably methyl, isobutyl, phenyl;

a primary, secondary or tertiary —NR'R" amine, wherein R' and R" the same or different represent a $C_1$ to $C_{10}$ alkyl group, preferably $C_1$ to $C_6$, linear or branched, preferably methyl;

a hydroxyl group;

or $R_4$, X" and $R_7$ form a heterocyclic group, preferably pyrrolidine;

or $R_1$, X' and $R_7$ form a phenol group;

or $R_1$, X', X", $R_7$ and $R_4$ form a polycyclic group formed of at least 3 saturated and/or unsaturated rings, or of at least 3 rings of which only one or two thereof is (are) aromatic and forming between them ortho- or ortho- and peri-condensed systems, preferably the phenanthroline group.

In one particular embodiment, the ligand L is selected in the group consisting of the ligands of general formula 1 wherein:

X', X", the same or different, are selected from the group comprising the nitrogen atom, the C=O group, the C=S group and the C—OH group;

$m_1$ to $m_8$ the same or different represent 0 or 1;

n represents 1 or 2;

$R_1, R_2, R_3, R_4, R_5, R_6, R_7$ and $R_8$, the same or different, are selected in the group consisting of:

a hydrogen atom;

a $C_1$ to $C_{10}$ alkyl group, preferably $C_1$ to $C_6$, linear or branched, preferably methyl, terbutyl;

an aryl group, preferably phenyl;

a primary, secondary or tertiary —NR'R" amine, wherein R' and R" the same or different represent a hydrogen atom, a $C_1$ to $C_{10}$ alkyl group, preferably $C_1$ to $C_6$, linear or branched, preferably methyl;

a hydroxyl group;

$R_7$ and $R_8$, the same or different, represent a hydrogen atom;

or $R_4$, $R_5$, X" and $R_7$ form a heterocyclic group, preferably pyrrolidine;

or $R_1$, X' and $R_7$ form a phenol group;

or $R_1$, X', X", $R_7$ and $R_4$ form a polycyclic group formed of at least 3 saturated and/or unsaturated rings, or of at least 3 rings of which only one or two thereof are aromatic and forming between them ortho- or ortho- and peri-condensed systems, preferably the phenanthroline group.

In one particular embodiment the ligand L is selected from the ligands of general formula I wherein:

X', X", the same or different, are selected in the group consisting of the nitrogen atom, the C=O group, the C=S group and the C—OH group;

$m_1$ to $m_8$ the same or different represent 0 or 1;

n represents 1 or 2;

$R_1, R_2, R_3, R_4, R_5, R_6, R_7$ and $R_8$, the same or different, are selected in the group consisting of:

a hydrogen atom;

a $C_1$ to $C_{10}$, alkyl group preferably $C_1$ to $C_6$, linear or branched, preferably methyl, terbutyl;

an aryl group, preferably phenyl;

a primary, secondary or tertiary —NR'R" amine, wherein R' and R" the same or different represent a hydrogen atom, a $C_1$ to $C_{10}$ alkyl group, preferably $C_1$ to $C_6$, linear or branched, preferably methyl;

a hydroxyl group;

$R_7$ and $R_8$, the same or different, represent a hydrogen atom; or $R_4$, X" and $R_7$ form a heterocyclic group, preferably pyrrolidine; or $R_1$, X' and $R_7$ form a phenol group; or $R_1$, X', X", $R_7$ and $R_4$ form a polycyclic group formed of at least 3 saturated and/or unsaturated rings, or of at least 3 rings of which only one or two thereof is (are) aromatic and forming between them ortho- or ortho- and peri-condensed systems, preferably the phenanthroline group.

In one particular embodiment, the ligand L is selected in the group consisting of the compounds of formula I

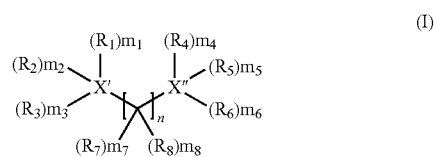

wherein

X', X", the same or different, are selected in the group consisting of the nitrogen atom, the C=O group, the C=S group and the C—OH group;

n represents 1;

$m_4$, $m_7$ and $m_8$ represent 1 $m_1$, $m_2$, $m_3$, $m_5$ and $m_6$ represent 0 or 1;

$R_1, R_2, R_3, R_5, R_6$, the same or different, are selected in the group consisting of:

a hydrogen atom;

a linear, branched or cyclic (mono- or polycyclic) hydrocarbon group comprising 1 to 20 carbon atoms, and possibly comprising one or more unsaturations in the form of double and/or triple bond(s), preferably methyl, isobutyl, phenyl;

a primary, secondary or tertiary —NR'R" amine, wherein R' and R" the same or different represents a $C_1$ to $C_{10}$ alkyl group, preferably $C_1$ to $C_6$, linear or branched, preferably methyl;

a hydroxyl group;

$R_8$ is H and $R_4$, X" and $R_7$ form a heterocyclic group, preferably pyrrolidine; or X', X", the same or different, are selected in the group consisting of the nitrogen atom, the C=O group, the C=S group and the C—OH group;

n represents 1;

$m_2$ to $m_6$ represent 0 or 1; $m_1$, $m_7$ and $m_8$ represent 1;

$R_1$ to $R_6$, the same or different, are selected in the group consisting of:

a hydrogen atom;

a branched, linear or cyclic (mono- or polycyclic) hydrocarbon group comprising 1 to 20 carbon atoms, and possibly comprising one or more unsaturations in the form of double and/or triple bond(s), preferably methyl, isobutyl, phenyl;

a primary, secondary or tertiary —NR'R" amine, wherein R' and R" the same or different represent a $C_1$ to $C_{10}$ alkyl group, preferably $C_1$ to $C_6$, linear or branched, preferably methyl;

a hydroxyl group;

$R_1$, X' and $R_7$ form a phenol group and $R_8$ represents H; or

X', X", the same or different, are selected in the group consisting of the nitrogen atom, the C=O group, C=S group and the C—OH group;

n represents 2;

$m_2$, $m_3$ $m_5$, $m_6$ and $m_8$ represent 0 or 1; $m_1$, $m_4$ and $m_7$ represent 1;

$R_2, R_3, R_5, R_6$ and $R_8$, the same or different, are selected in the group consisting of:

a hydrogen atom;

a branched, linear or cyclic (mono- or polycyclic) hydrocarbon group comprising 1 to 20 carbon atoms and possibly comprising one or more unsaturations in the form of double and/or triple bond(s), preferably methyl, isobutyl, phenyl;

a primary, secondary or tertiary —NR'R" amine, wherein R' and R" the same or different represent a $C_1$ to $C_{10}$ alkyl group, preferably $C_1$ to $C_6$, linear or branched, preferably methyl;

a hydroxyl group;

$R_1$, X', X", $R_7$ and $R_4$ form a polycyclic group comprising 3 saturated and/or unsaturated rings, or at least 3 rings of which one or two thereof are aromatic and form between them ortho- or ortho- and peri-condensed systems, preferably the phenanthroline group.

In one particular embodiment, the ligand L is selected in the group consisting of the ligands of general formula I wherein X' and X" both the same represent the C═O group, and $m_2$, $m_3$, $m_5$ and $m_6$ are zero, $m_1$ and $m_4$ equal 1, $m_1$, $m_2$ and $m_3$ and $R_1$, $R_2$, $R_3$ and $m_4$, $m_5$, $m_6$ and $R_4$, $R_5$, $R_6$ all being interchangeable, $m_7$ and $m_8$ represent 0 or 1, $R_1$ and $R_4$ the same or different are selected in the group consisting of:
  a $C_1$ to $C_{10}$ alkyl group, preferably $C_1$ to $C_6$, linear or branched, preferably methyl, terbutyl;
  an aryl group, preferably phenyl;
  a primary, secondary or tertiary —NR'R" amine, wherein R' and R" the same or different represent a hydrogen atom, a $C_1$ to $C_{10}$ alkyl group, preferably $C_1$ to $C_6$, linear or branched, preferably methyl;

$R_7$ and $R_8$ represent a hydrogen atom.

In one particular embodiment, the ligand L is selected in the group consisting of the ligands of general formula I wherein X' represents a C═O group and X" represents the nitrogen atom, or X' represents the nitrogen atom and X" represents a C═O group, and if X'═C═O: $m_2$, $m_3$, $m_6$, $m_8$ are zero, $m_1$, $m_4$, $m_5$ and $m_7$ equal 1 and n equals 1;
  $R_1$ represents a hydroxyl group;
  $R_7$ represents a hydrogen atom;
  $R_4$, $R_5$, $R_7$ and X" form a pyrrolidine group;

if X"═C═O: $m_5$, $m_6$, $m_3$ and $m_8$ are zero, $m_1$, $m_2$, $m_3$, $m_4$ m and $m_7$ equal 1 and n equals 1;
  $R_4$ represents a hydroxyl group;
  $R_7$ represents a hydrogen atom;
  $R_1$, $R_2$, $R_7$ and X' form a pyrrolidine group.

In one particular embodiment, the ligand L is selected in the group consisting of the ligands of formula I wherein X' and X" represent a nitrogen atom, and n equals 2;

$m_3$ and $m_6$ are zero, $m_1$, $m_2$, $m_4$, $m_5$, $m_7$ and $m_8$ equal 0 or 1;

$R_1$, $R_2$, $R_4$ and $R_5$, the same or different, are selected in the group consisting of:
  a hydrogen atom;
  a $C_1$ to $C_{10}$ alkyl group, preferably $C_1$ to $C_6$, linear or branched, preferably methyl;
  or $R_1$, X', X", $R_7$ and $R_4$ form a polycyclic group formed of at least 3 saturated and/or unsaturated rings, or of at least 3 rings of which only one or two thereof are aromatic and forming between them ortho- or ortho- and peri-condensed systems, preferably the phenanthroline group.

In one particular embodiment the ligand L is selected in the group consisting of the ligands of general formula I wherein X' represents the C—OH group and X" represents the C═O group, or X' represents the C═O group and X" represents the C—OH group, and if X'═C═O: $m_2$, $m_3$, $m_5$, $m_6$, $m_8$ are zero, $m_1$, $m_4$, and $m_7$ equal 1 and n equals 1;
  $R_1$ represents a $C_1$ to $C_{10}$ alkyl group, preferably $C_1$ to $C_6$, linear or branched, preferably methyl;
  $R_4$, $R_7$ and X" form a phenol group;

if X"═C═O: $m_5$, $m_6$, $m_8$, $m_2$, $m_3$, are zero, $m_1$, $m_4$ and $m_7$ equal 1 and n equals 1;
  $R_4$ represents a $C_1$ to $C_{10}$ alkyl group, preferably $C_1$ to $C_6$, linear or branched, preferably methyl;
  $R_1$, $R_7$ and X' form a phenol group.

In one embodiment, the ligand L is represented by formula II

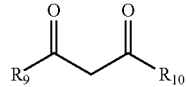

Formula II wherein:

$R_9$, $R_{10}$, the same or different, represent a branched, linear or cyclic (mono or polycyclic) hydrocarbon group comprising 1 to 20 carbon atoms and possibly comprising one or more unsaturations in the form of double and/or triple bond(s), preferably methyl, isobutyl, phenyl; or a primary, secondary or tertiary NR'R" amine, wherein R'R" the same or different represent a $C_1$ to $C_{10}$ alkyl group, preferably $C_1$ to $C_6$, linear or branched, preferably methyl.

In one embodiment, the ligand L is represented by formula III

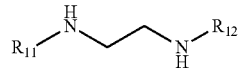

Formula III wherein $R_{11}$ and $R_{12}$, the same or different represent a hydrogen atom or a branched, linear or cyclic (mono- or polycyclic) hydrocarbon group comprising 1 to 20 carbon atoms and possibly comprising one or more unsaturations in the form of double and/or triple bond(s), preferably methyl, isobutyl, phenyl.

In one embodiment, the ligand L is represented by formula IV

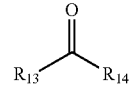

Formula IV wherein:

$R_{13}$ represents a branched, linear or cyclic (mono- or polycyclic) hydrocarbon group comprising 1 to 20 carbon atoms and possibly comprising one or more unsaturations in the form of double and/or triple bond(s), preferably methyl, isobutyl, phenyl; or a hydroxyl group, and $R_{14}$ represents a heterocyclic group preferably pyrrolidine or a phenol group.

In one preferred embodiment, the ligand L is selected in the group consisting of the following compounds:

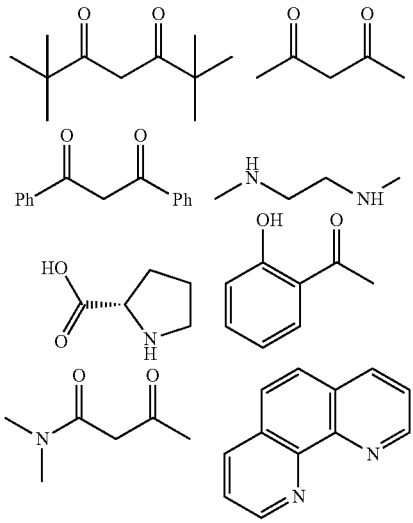

In one embodiment, the ligand L is:

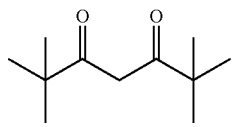

In one embodiment, the ligand L is:

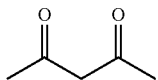

In one embodiment, the ligand L is:

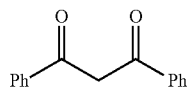 [SMILES: O=C(CC(=O)c1ccccc1)c1ccccc1]

In one embodiment, the ligand L is:

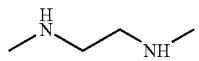

In one embodiment, the ligand L is:

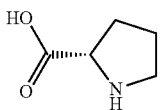

In one embodiment, the ligand L is:

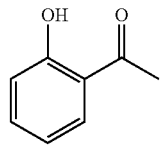

In one embodiment, the ligand L is:

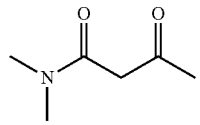

In one embodiment, the ligand L is:

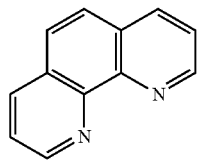 [SMILES: c1cnc2c(c1)ccc1cccnc12]

The following definitions are valid for the whole of the description unless otherwise indicated:
- <<alkyl>> or <<alkyl->> represents a saturated hydrocarbon radical, linear or branched, comprising 1 to 10 carbon atoms, preferably 1 to 6 carbon atoms and in particular the methyl, ethyl radical, the propyl, butyl, pentyl, hexyl, heptyl, octyl, nonyl and decyl radicals;
- <<aryl>> or <<aryl->> represents an aromatic, mono- or polycyclic hydrocarbon radical, and for example the phenyl radical or the naphtyl radical;
- <<hydrocarbon radical>> represents a branched, linear or cyclic (mono- or polycyclic) hydrocarbon radical comprising 1 to 20 carbon atoms and possibly comprising one or more unsaturations in the form of double and/or triple bond(s), for example but not limited thereto methyl, ethyl, propyl, isopropyl, butyl, isobutyl, sec-butyl, tert-butyl, cyclohexyl, benzyl, phenyl, vinyl, allyl, and others;
- <<hydroxyl>> or <<hydroxy->> represents the OH group;
- <<halogen>> designates fluorine, chlorine, bromine and iodine;
- <<alkoxy>> represents an alkyl group linked to an oxygen, alkyl having the above-mentioned definition. As an example mention may be made of methoxy, ethoxy etc.
- <<esters>> represents a —COOR group, R being selected in the group consisting of the alkyls, alkyl having the above-mentioned definition.

All the radicals whose definitions are given above may optionally be substituted by one or more halogen atoms where halogen has the above-mentioned definition, by one or more alkyl radicals, by one or more hydroxy, aryl, amino radicals, the substituents possibly being the same or different.

The copper-based catalysts used in the invention are selected in the group consisting of metallic coppers, copper (I) oxides or copper (II) oxides, copper (I) or copper (II) hydroxides, copper (I) or copper (II) inorganic or organic salts and the complexes of copper (I) or copper (II) with the usual ligands.

Preferred examples of copper-based catalysts include but are not limited thereto, copper (0), copper halides (e.g. copper (I) iodides, copper (I) bromide, copper (II) bromide, copper (I) chloride, copper (II) chloride, copper oxides or hydroxides (e.g. copper (I) oxide, copper (II) oxide, copper (II) hydroxides), copper nitrates (e.g. copper (I) nitrate, copper (II) nitrates), copper sulfates or sulfites (e.g. copper (I) sulfate, copper (II) sulfate (II) copper (I) sulfite) the organic salts of copper in which the counter-ion has at least one carbon atom (e.g. copper (II) carbonate, copper (I) acetate, copper (II) acetate, copper (II) trifluoromethylsulfonate, copper (I) methylate, copper (II) methylate, copper (II) acetylacetonate).

Preferred copper-based catalysts are copper (0), copper (I) iodide (CuI), copper (II) oxide (CuO), copper (II) acetylacetonate [Cu(acac)$_2$], CuI+Cu(acac)$_2$.

In one preferred embodiment, the copper-based catalyst is copper iodide CuI.

In one particular embodiment of the invention, the method is conducted at a temperature lower than 150° C.

In one embodiment of the invention, X is selected in the group consisting of bromine and iodine.

In one particular embodiment of the invention X represents iodine.

In this particular embodiment, R is selected in the group consisting of the acceptor inductive effect groups and the donor mesomer effect groups.

In one particular embodiment of the invention X represents bromine.

In this particular embodiment, R is an acceptor inductive effect group.

In one particular embodiment of the invention the method is conducted in two steps according to the following reaction scheme:

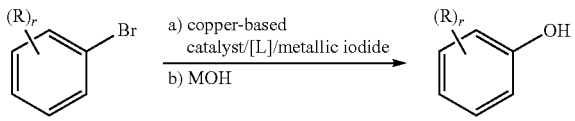

The first step (a) corresponds to a nucleophilic substitution of bromobenzene by a metallic iodide in the presence of a copper-based catalyst and a ligand.

The second step corresponds to the hydroxylation reaction of the invention in the presence of copper-based catalyst and a ligand.

In one embodiment, the two-step method is implemented with R representing a donor mesomer effect group.

In this embodiment, the molar ratio between the number of moles of metallic iodide and the number of moles of brominated compound varies between 0.1 and 4 and preferably between 1 and 3.

In one embodiment of the invention, the metallic iodide is selected in the group consisting of NaI, KI or CsI, preferably the metallic iodide is NaI By acceptor inductive effect group is meant a group selected from the group comprising the NO$_2$ group, the esters, the CN group, a halogen atom, an alkoxy group.

In one preferred embodiment, the acceptor inductive effect group is selected from the group comprising the NO$_2$ group, the CO$_2$Me group, the CN group, the fluorine atom, bromine atom, iodine atom, chlorine atom, methoxy group.

By donor mesomer effect group is meant a group selected in the group consisting of the phenyl group, the hydroxy group (OH), a $C_1$ to $C_{10}$ alkyl, preferably $C_1$ to $C_6$, linear or branched, a halogen atom, a hydrogen atom, an alkoxy group, or R together with the phenyl forms a naphtyl derivative.

In one preferred embodiment, the donor mesomer effect group is selected in the group consisting of the phenyl group, the hydroxyl group, the methyl group, the fluorine atom, hydrogen atom, the methoxy group or R together with the phenyl forms a naphtyl derivative.

In one preferred embodiment of the invention, the cation M is selected in the group consisting of the potassium salts and cesium salts.

The molar ratio between the number of moles of copper-based catalyst and the number of moles of halogenated aryl compound is preferably between 0.001 and 0.5, preferably between 0.05 and 0.2.

The molar ratio between the number of moles of ligand L and the number of moles of halogenated aryl compound varies between 0.001 and 0.9; preferably between 0.1 and 0.7.

In one embodiment, the molar ratio between the number of moles of MOH and the number of moles of halogenated aryl compound varies between 0.1 and 5, preferably between 2 and 4.

In one embodiment, the method of the invention is conducted in the presence of a solvent.

The solvent is selected from the group formed of water, the organic solvents and mixtures thereof.

In one embodiment, the organic solvent is selected in the group consisting of:
  linear or cyclic carboxamides, preferably N-dimethylacetamide (DMAC), N, N-diethylacetamide, dimethylformamide (DMF), diethylformamide or 1-methyl-2-pyrrolidinone (NMP);
  dimethylsulfoxide (DMSO);
  hexamethylphosphotriamide (HMPT);
  tetramethylurea;
  benzene;
  nitro-based compounds, preferably nitromethane, nitroethane, 1-nitropropane, 2-nitropropane or nitrobenzene;
  aliphatic or aromatic nitriles, preferably acetonitrile, propionitrile, butanenitrile, isobutanenitrile, pentanenitrile, 2-methylglutaronitrile or adiponitrile;
  tetramethylene sulfone;
  organic carbonates, preferably dimmethylcarbonate, diisopropylcarbonate or di-n-butylcarbonate;
  alkylated esters, preferably ethyl acetate or isopropyl acetate;
  aliphatic or aromatic ethers, preferably 1,4-dioxane;
  halogenated or non-halogenated hydrocarbon compounds, preferably toluene or chlorobenzene;
  ketones, preferably acetone, methylethylketone, methylisobutylketone (MIBK), cyclopentanone, cyclohexanone;
  heterorings comprising a nitrogen group, preferably pyridine, picoline or quinolines;
alone or in a mixture.

In one preferred embodiment, the solvent is a water/DMSO mixture. In this embodiment the water/DMSO ratio is between 7:1 and 1:7, preferably between 1:1 and 1:3.

In one preferred embodiment, the method is conducted in 2 steps, the solvent of step a) is preferably 1,4-dioxane and the solvent of step b) being water.

In one particular embodiment, the reaction time is less than 40 hours, preferably between 12 and 36 hours, preferably between 24 and 36 hours.

In one particular embodiment, the reaction time of step a) of the method implemented in two steps is less than 10 hours.

In one particular embodiment, the method implemented by the invention also produces a biarylether (2), preferably biphenylether. This particular embodiment corresponds to the following scheme:

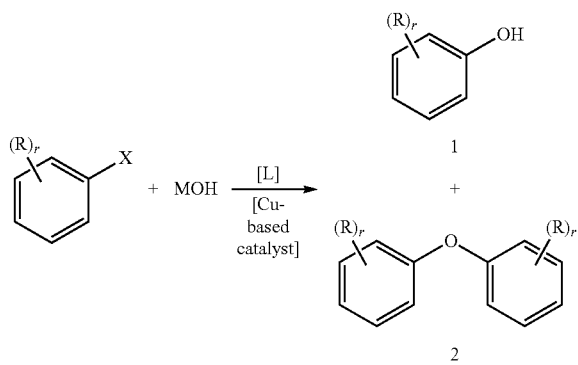

M, R, r and L having the above-mentioned definitions.

In this embodiment, the copper-based catalyst is preferably CuI, X preferably represents the iodine atom and L is preferably di-tert-butyl ketone, M, R and r having the above-mentioned definitions.

In another particular embodiment of the invention, the method is performed in the absence of the copper-based catalyst. This embodiment corresponds to the following scheme:

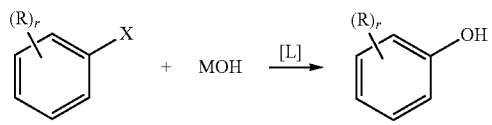

wherein R, r, X, M and L have the above-mentioned definitions.

In this particular embodiment, X represents an iodine or bromine atom and R, r, M and L have the above-mentioned definitions.

The present invention and its different embodiments will be better understood on reading the following examples. These examples are given by way of indication and are non-limiting.

General Operating Protocol

All the reactions are carried out in 35 ml Schlenk tubes or in a carousel: <<RR98030 Radley Tube Reaction Station>> under a pure, dry nitrogen atmosphere.

DMSO (dimethyl sulfoxide) is distilled and stored over a 4 Å activated molecular sieve under a nitrogen atmosphere. The other solvents are distilled and stored under a nitrogen atmosphere.

The cesium carbonate (Alfa Aesar), monohydrated cesium hydroxide (Alfa Aesar) and copper iodide, CuI (Aldrich) and all the other solid materials are stored in the presence of $P_4O_{10}$ in a dissector under a vacuum at ambient temperature. The (98%+) 2,2, 6,6-tetramethyl-3,5 heptanedione (Alfa Aesar) and other ligands are obtained from commercial sources (Aldrich, Acros, Alfa Aesar, Fluka, Lancaster) and used without additional purification.

The Iodophenyls and Bromophenyls are obtained from commercial sources. If these are solids, they are recrystallized in a suitable solvent. (Reference D D Perrin, W. L. F. Amarego, D. R. Perrin, Purification of Laboratory Chemicals, 3rd edition; Pergamon Press: New York, 1985). If these are liquids they are distilled in vacuo and stored under a nitrogen atmosphere.

Column chromatographies are performed using silica gel: SDS 60 A. C. (35-70 μm). Thin layer chromatographies are carried out using MERCK 60F254 silica gel plates.

All the products are characterized by their NMR, CG/MS and HRMS spectra. NMR spectra are recorded at 20° C. on Bruker AC 400 MHz apparatus or on DRX-250 spectrometer operating respectively at 400 MHz for $^1H$ and at 100 MHz for $^{13}C$. The chemical shifts are given in ppm/TMS for $^1H$ hydrogen and for $\{^1H\}$ $^{13}C$ (δ 77.00 for C). The first order peak patterns are indicated as s (singlet), d (doublet), t (triplet), q (quadruplet). The complex signals which are not of first order are indicated as m (multiplet).

Gas phase chromatographies and mass spectra (GC/MS) are recorded on Agilent Technologies 6890 N instrument with Agilent 5973 N (Ei) mass detector and apolar capillary column HP5-MS 30 m×0.25 mm (stationary phase: 5% diphenyldimethylpolysiloxane film, 0.25 μm). GC/MS protocol: initial temperature 45° C.; initial time 2 min; slope of temperature curve: 2° C./min up to 50° C. then 10° C./min; final temperature 250° C.; final time: 10 nm.

The IR spectra are recorded on Nicolet 210 FT-IR apparatus (in the form of a thin film for the liquid products and KBr pellet or in a solution of carbon tetrachloride for the solid products). The mass spectra FAB+ and HRMS are recorded on a JEOL JMS-DX300 spectrophotometer (3 keV, xenon) in a nitrobenzyl alcohol matrix.

EXAMPLE A

Method for the Hydroxylation of Iodinated or Brominated Aryl Compounds in the Presence of a Catalytic System Comprising Copper Iodide and Dibenzoylmethane

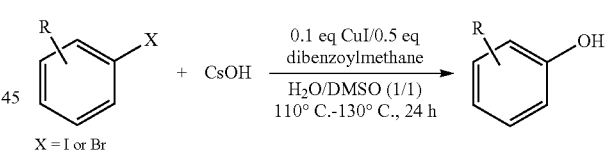

Operating Mode of Example A:

After standard purging and filling cycles with pure, dry nitrogen a Radley tube (Carousel RR98030" reaction station) or oven-dried Schlenk tube equipped with magnetic stir bar is charged with CuI (0.1 eq.), CsOH.H2O (3 eq.), halogenophenyl if it is a solid (1 mmol, 1 eq.) and dibenzoylmethane (0.5 eq.).

The tube is then purged and re-filled with nitrogen. If it is a liquid the halogenophenyl is added under a stream of nitrogen using a syringe at ambient temperature, followed by anhydrous, degassed DMSO (1.0 mL) and 1 mL of degassed water. The tube is sealed under positive nitrogen pressure, left under stirring and heated to 130° C. (or 110° C. if so specified) for 24 hours. After cooling to ambient temperature, 10 mL dichloromethane are added and 1 mL HCl (37%).

The mixture is left under stirring for two hours, 130 μL of 1,3-dimethoxybenzene (internal standard) are added. A small sample of the reaction mixture is taken and filtered through a Celite® pad, the solid is then washed with dichloromethane. The filtrate is analyzed by gas chromatography.

The filtrate is washed twice with water. The aqueous phases are combined and extracted with dichloromethane five times. The organic phases are combined, dried over sodium sulfate, filtered and concentrated in vacuo to yield the raw product. The raw product obtained is then purified by silica gel chromatography with a mixture of heptane and ethyl acetate.

The products are characterized by NMR. Their gas chromatography yields are determined with factor correction using authentic samples of the expected products.

To test the extent of the hydroxylation reaction, various tests were conducted starting from iodinated or brominated aryl compounds carrying either electro-attractor or electro-donor substituents.

The results are given in Table 1.

TABLE 1

| Example No. | ArX | ArOH | Yield [%][a] |
|---|---|---|---|
| 1 | PhI | PhOH | 97 |
| 2 | $O_2N$—C$_6$H$_4$—I | $O_2N$—C$_6$H$_4$—OH | 22b, 90c |
| 3 | 4-acetyl-C$_6$H$_4$—I | 4-acetyl-C$_6$H$_4$—OH | 90c |
| 4 | NC—C$_6$H$_4$—I | NC—C$_6$H$_4$—OH | 91c |
| 5 | Ph—C$_6$H$_4$—I | Ph—C$_6$H$_4$—OH | 95 |
| 6 | F—C$_6$H$_4$—I | F—C$_6$H$_4$—OH | 70 |
| 7 | Cl—C$_6$H$_4$—I | Cl—C$_6$H$_4$—OH | 75, 95d |
| 8 | Br—C$_6$H$_4$—I | Br—C$_6$H$_4$—OH | 84 |
| 9 | 1,2-diiodobenzene | C$_6$H$_5$—OH | 95 |
| 10 | HO—C$_6$H$_4$—I | C$_6$H$_5$—OH | 95 |
| 11 | MeO—C$_6$H$_4$—I | MeO—C$_6$H$_4$—OH | 90 |
| 12 | Me—C$_6$H$_4$—I | Me—C$_6$H$_4$—OH | 82 |
| 13 | 2-iodotoluene | 2-methylphenol | 84 |

TABLE 1-continued

| Example No. | ArX | ArOH | Yield [%][a] |
|---|---|---|---|
| 14 | | | 96, 71[c] |
| 15 | | | 84 |
| 16 | | | 78, 7[b] |
| 17 | | | 83, 17[b] |
| 18 | | | 82[c], 27[b] |
| 19 | | | 84, 20[b] |
| 20 | | | 94, 24[b] |

The yields correspond to the isolated yields

The reaction was conducted under the following conditions of time and temperature:

[a]: 24 hours at 130° C.

[b]: 24 hours at 130° C. in the absence of copper bdide

[c]: 24 hours at 110° C.

[d]: 36 hours at 130° C.

The characterization of the compounds obtained and the details of the operating modes followed are detailed below.

EXAMPLE 1

Phenol

Following general operating mode A, iodobenzene (112 µL, 1.0 mmol) was reacted with cesium hydroxide to give the expected product in the form of a white solid with a yield of 97% (eluent: ethyl acetate/heptane 20:80).

Identification

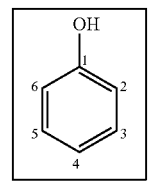

$^1$H NMR (400 MHz, CDCl$_3$): δ 7.15-7.19 (t, 1H, H$_4$), 7.84-7.88
(t, 2H, H$_{3, 5}$), 6.75-6.77 (d, 2H, H$_{2, 6}$), 4.94 (1H, OH).
$^{13}$C NMR (100 MHz, CDCl$_3$): δ 155 (C$_1$), 129.73 (C$_{3, 5}$), 120.88 (C$_4$), 1115.33 (C$_{2, 6}$).
GC/MS: rt=8.96 min, M/Z=94.
HRMS: 95.0502 (M+H). Theoretical: 95.0419

EXAMPLES 2 AND 18

4-Nitrophenol

Following general operating mode A, 1-iodo-4-nitrobenzene or 1-bromo-4-nitrobenzene (249 mg or 202 mg, 1.0 mmol) were reacted at 110° C. with cesium hydroxide to obtain the expected product in the form of a yellow solid with respective yields of 90% and 82% (ethyl acetate/heptane 20:80).
Identification

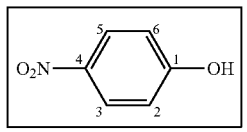

$^1$H NMR (400 MHz, CDCl$_3$): δ 8.12 (m, 2H, H$_{3, 5}$), 6.87 (m, 2H, H$_{2, 6}$), 6.10 (1H, OH).
$^{13}$C NMR (100 MHz, CDCl$_3$): δ 160.31 (C$_1$), 134.37 (C$_{3, 5}$), 113.51 (C$_{2,6}$) 102.78 (C$_4$).
GC/MS: rt=16.84 min, M/Z=139.
HRMS: 140.0331 (M+H). Theoretical: 140.0348

EXAMPLES 3 AND 19

4'-Hydroxyacetophenone

Following general operating mode A, 4'-iodoacetophenone or 4'-bromo acetophenone (246 mg or 199 mg, 1.0 mmol) were reacted with cesium hydroxide at respectively 110 or 130° C. to afford the expected product in the form of a white solid at respective yields of 90% and 84% (eluant: ethyl acetate/heptane 20:80).
Identification

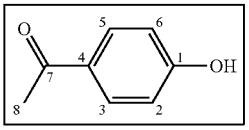

$^1$H NMR (400 MHz, CDCl$_3$): δ 6.70-6.71 (m, 4H, H$_{2, 3}$), 4.44 (1H, OH), 3.69 (s, 3H, H$_8$).
$^{13}$C NMR (100 MHz, CDCl$_3$): δ 154.06 (C$_{1, 4}$), 149.55 (C$_7$), 116.09 (C$_{3, 5}$), 114.84 (C$_{2, 6}$), 56.02 (C$_8$).
GC/MS: rt=15.97 min, M/Z=136.
HRMS: 135.0452 (M−H). Theoretical: 135.0446

EXAMPLES 4 AND 20

4-Hydroxybenzonitrile

Following general operating mode A, 4-iodobenzonitrile or 4-bromobenzonitrile (229 mg or 182 mg, 1.0 mmol) were reacted at respectively 110° C. or 130° C. with cesium hydroxide to afford the expected product in the form of a white solid at respective yields of 91% and 94% (eluent: ethyl acetate/heptane 20:80).
Identification

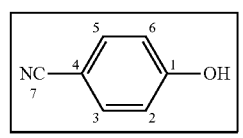

$^1$H NMR (400 MHz, CDCl$_3$): δ 7.47-7.50 (m, 2H, H$_{3, 5}$), 6.83-6.86 (m, 2H, H$_{2, 6}$), 5.97 (1H, NH).
$^{13}$C NMR (100 MHz, CDCl$_3$): δ 159.79 (C$_1$), 134.33 (C$_{3, 5}$), 129.39 (C$_7$), 116.41 (C$_{2,6}$), 103.71 (C$_4$).
GC/MS: rt=16.13 min, M/Z=119.
HRMS: 118.0293 (M−H). Theoretical: 118.0293

EXAMPLE 5

Biphenyl-4-ol

Following general operating mode A, 4-iodophenyl (280 mg, 1.0 mmol) was reacted with cesium hydroxide to give the expected product in the form of a brown solid with a yield of 95% (eluent: ethyl acetate/heptane 20:80).
Identification

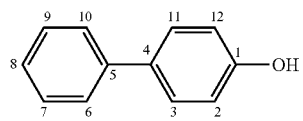

$^1$H NMR (400 MHz, CDCl$_3$):
δ 7.45-7.47 (m, 2H, H$_{6, 10}$), 7.39-7.42 (m, 2H, H$_{3, 11}$), 7.31-7.36 (m, 2H, H$_{7, 9}$), 7.21-7.24 (m, 1H, H$_8$), 6.83-6.85 (m, 2H, H$_{2, 12}$), 5.10 (1H, OH).
$^{13}$C NMR (100 MHz, CDCl$_3$): δ 155.24 (C$_1$), 140.83 (C$_5$), 134.00 (C$_4$), 128.76 (C$_{7, 9}$), 128.41 (C$_{3, 11}$), 126.71 (C$_{6, 10}$), 115.71 (C$_{2, 12}$).
GC/MS: rt=21.03 min, M/Z=170.
HRMS: 169.0649 (M−H). Theoretical: 169.0653.

EXAMPLE 6

4-fluorophenol

Following general operating mode A, 4-fluoroiodobenzene (222 mg, 1.0 mmol) was reacted with cesium hyroxide to give the expected product in the form of a white solid with a yield of 70% (eluent: ethyl acetate/heptane 20:80).
Identification

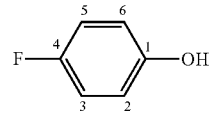

$^1$H NMR (400 MHz, CDCl$_3$): δ 6.83-6.87 (d, 2H, H$_{3, 5}$), 6.68-6.71 (d, 2H, H$_{2, 6}$), 4.66 (1H, OH).
$^{13}$C NMR (100 MHz, CDCl$_3$): δ 154.86 (C$_1$), 132.54 (C$_{3, 5}$), 117.25 (C$_{2, 6}$), 113.15 (C$_4$).
GC/MS: rt=12.86 min, M/Z=112.
HRMS: 113.0403 (M+H). Theoretical: 113.0403

EXAMPLE 7

4-Chlorophenol

Following general operating mode A, 4-chloroidobenzene (250 mg, 1.0 mmol) was reacted with cesium hydroxide to give the expected product in the form of a white solid with a yield 75% (eluent: ethyl acetate/heptane 10:90).

Identification

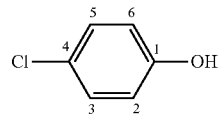

$^1$H NMR (400 MHz, CDCl$_3$): δ 7.07-7.09 (d, 2H, H$_{3,\,5}$), 6.65-6.68 (d, 2H, H$_{2,\,6}$), 5.41 (1H, OH).
$^{13}$C NMR (100 MHz, CDCl$_3$): δ 154.14 (C$_1$), 129.64 (C$_{3,\,5}$), 125.9 (C$_4$), 116.46 (C$_{2,\,6}$).
GC/MS: rt=13.09 min, M/Z=128.
HRMS: 129.0128 (M+H). Theoretical: 129.0107

EXAMPLE 8

4-Bromophenol

Following general operating mode A, 4-iodobromobenzene (282 mg, 1.0 mmol) was reacted with cesium hydroxide to give the expected product in the form of a brown solid with a yield of 84% (eluent: ethyl acetate/heptane 20:80).
Identification

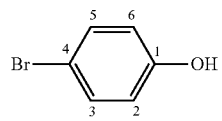

$^1$H NMR (400 MHz, CDCl$_3$): δ 7.23-7.26 (d, 2H, H$_{3,\,5}$), 6.63-6.65 (d, 2H, H$_{2,\,6}$), 5.05 (1H, OH).
$^{13}$C NMR (100 MHz, CDCl$_3$): δ 154.86 (C$_1$), 132.54 (C$_{3,\,5}$), 117.25 (C$_{2,\,6}$), 113.15 (C$_4$).
GC/MS: rt=14.06 min, M/Z=172.
HRMS: 170.9446 (M−H). Theoretical: 170.9446

EXAMPLE 11

4-methoxyphenol

Following general operating mode A, 4-methoxyiodobenzene (246 mg, 1.0 mmol) is caused to react with cesium hydroxide to give the expected product in the form of a white solid with a yield of 90% (eluent: ethyl acetate/heptanes 20:80).
Identification

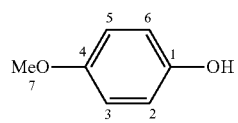

$^1$H NMR (400 MHz, CDCl$_3$): δ 6.68-6.69 (m, 3H, H$_{2,3,5,6}$), 5.38 (1H, OH), 3.67 (s, 3H, H$_7$).
$^{13}$C NMR (100 MHz, CDCl$_3$): δ 153.80 (C$_1$), 149.68 (C$_1$), 116.13 (C$_{3,\,5}$), 114.95 (C$_{2,\,6}$), 55.89 (C$_7$).
GC/MS: rt=12.71 min, M/Z=124.
HRMS: 125.0617 (M+H). Theoretical: 125.0603

EXAMPLE 12 p-Cresol

Following general operating mode A, 4-iodotoluene (218 mg, 1.0 mmol) was reacted with cesium hydroxide to give the expected product in the form of a white solid with a yield of 82% (eluent ethyl acetate/heptane 20:80).
Identification

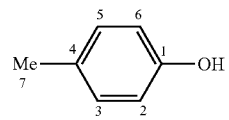

$^1$H NMR (400 MHz, CDCl$_3$): δ 6.89-6.91 (d, 2H, H$_{3,\,5}$), 6.61-6.63 (d, 2H, H$_{2,\,6}$), 5.86 (1H, OH), 2.15 (s, 3H, H$_7$).
$^{13}$C NMR (100 MHz, CDCl$_3$): δ 153.15 (C$_1$), 130.08 (C$_4$), 130.08 (C$_{3,\,5}$), 115.08 (C$_{2,\,6}$), 20.04 (C$_7$).
GC/MS: rt=10.56 min, M/Z=108.
HRMS: 109.0668 (M+H). Theoretical: 109.0653

EXAMPLE 13 o-Cresol

Following general operating mode A, 2-methyliodobenzene (128 µL, 1.0 mmol) was reacted with cesium hydroxide to give the expected product in the form of a white solid with a yield of 84% (eluent: ethyl acetate/heptane 20:80).
Identification

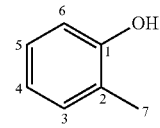

$^1$H NMR (400 MHz, CDCl$_3$): δ 6.95-7.03 (m, 2H, H$_{4,\,5}$), 6.73-6.77 (m, 1H, H$_3$), 6.64-6.67 (m, 1H, H$_6$), 5.01 (1H, OH), 2.15 (s, 3H, H$_7$).
$^{13}$C NMR (100 MHz, CDCl$_3$): δ 153.93 (C$_1$), 131.22 (C$_3$), 127.23 (C$_s$), 124.04 (C$_2$), 120.98 (C$_4$), 115.27 (C$_6$), 15.90 (C$_7$).
GC/MS: rt=10.68 min, M/Z=108.
HRMS: 107.0499 (M−H). Theoretical: 107.0497

EXAMPLE 14

3,5-dimethylphenol

Following general operating mode A, 3,5-dimethyliodobenzene (145 µL, 1.0 mmol) was reacted with cesium hydroxide to give the expected product in the form of a white solid with a yield of 96% (eluent: dichloromethane/heptane 20:80).

Identification

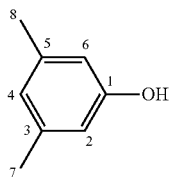

$^1$H NMR (400 MHz, CDCl$_3$): δ 6.50 (s, 1H, H$_4$), 6.38 (s, 2H, H$_{2,6}$), 4.67 (1H, OH), 2.17 (d, 6H, H$_{7,8}$).
$^{13}$C NMR (100 MHz, CDCl$_3$): δ 155.53 (C$_1$), 139.72 (C$_{3,5}$), 122.71 (C$_4$), 113.15 (C$_{2,6}$), 21.48 (C$_{7,8}$).
GC/MS: rt=12.21 min, M/Z=122.
HRMS: 123.0816 (M+H). Theoretical: 123.0810

EXAMPLE 15 m-Cresol

Following general operating mode A, 3-methyliodobenzene (128 µL, 1.0 mmol) was reacted with cesium hydroxide to give the expected product in the form of a white solid with a yield of 84% (eluent: ethyl acetate/heptane 20:80).
Identification

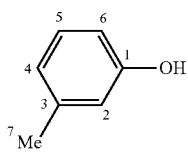

$^1$H NMR (400 MHz, CDCl$_3$): δ 7.52-7.54 (d, 2H, H$_{4,6}$), 6.69 (s, 1H, H$_2$), 6.34-6.36 (m, 1H, H$_5$), 4.89 (1H, OH), 2.29 (s, 3H, H$_7$).
$^{13}$C NMR (100 MHz, CDCl$_3$): δ 156.33 (C$_1$), 142.64 (C$_3$), 139.59 (C$_5$), 117.40 (C$_4$), 115.14 (C$_{2,6}$), 28.12 (C$_7$).
GC/MS: rt=10.88 min, M/Z=108.
HRMS: 107.0498 (M−H). Theoretical: 107.0409

EXAMPLE 16

3-Nitrophenol

Following general mode A, 1-bromo-3-nitrobenzene (202 mg, 1.0 mmol) was reacted with cesium hydroxide to give the expected product in the form of a red solid with a yield of 78% (eluent: ethyl acetate/heptane 20:80).
Identification

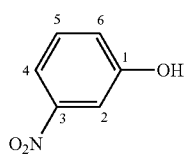

$^1$H NMR (400 MHz, CDCl$_3$): δ 7.72-7.74 (m, 1H, H$_5$), 7.64-7.65 (m, 1H, H$_4$), 7.31-7.35 (t, 1H, H$_6$), 7.12-7.14 (m, 1H, H$_2$), 5.40 (1H, OH).

$^{13}$C NMR (100 MHz, CDCl$_3$): δ 156.33 (C$_1$), 149.15 (C$_3$), 130.42 (C$_5$), 122.18 (C$_6$), 115.93 (C$_4$) 110.62 (C$_2$).
GC/MS: rt=16.35 min, M/Z=139.
HRMS: 138.0194 (M−H). Theoretical: 138.0191

EXAMPLE 17

2'-Hydroxyacetophenone

Following general operating mode A, 2'-bromoacetophenone (199 mg, 1.0 mmol) was reacted with cesium hydroxide to give the expected product in the form of an oil with a yield of 83% (eluent: ethyl acetate/heptane 20:80).
Identification

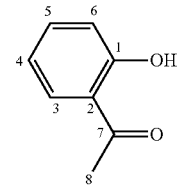

$^1$H NMR (400 MHz, CDCl$_3$): δ 12.19 (s, 1H, OH), 7.64-7.68 (m, 1H, H$_5$), 7.31-7.41 (m, 1H, H$_3$), 6.88-6.90 (m, 1H, H$_4$), 6.80-6.84 (m, 1H, H$_6$), 2.55 (s, 3H, H$_8$),
$^{13}$C NMR (100 MHz, CDCl$_3$): δ 204.82 (C$_7$), 162.44 (C$_1$), 136.66 (C$_5$), 130.69 (C$_3$), 119.66 (C$_2$), 118.99 (C$_4$), 118.60 (C$_6$), 26.93 (C$_8$).
GC/MS: rt=15.32 min, M/Z=136.
HRMS: 135.0444 (M−H). Theoretical: 135.0446

EXAMPLE B

Method for the Hydroxylation of Brominated Aryl Compounds in the Presence of Sodium Iodide and a Catalytic System Comprising Copper Iodide and N,N'-dimethylethylenediamine

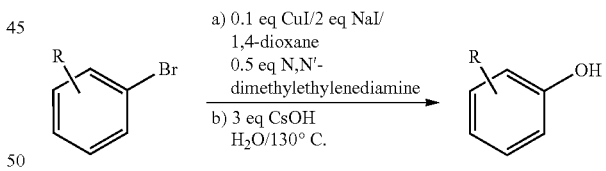

Operating Mode of Example B:
After standard purging and filling cycles with pure, dry nitrogen, a Radley tube (RR98030 Carousel Reaction Station) or an oven-dried Schlenk tube equipped with magnetic stir bar is charged with CuI (0.1 eq.), NaI (2 eq) and phenyl bromide, if it is a solid (1 mmol, 1 eq). The tube is then purged and re-filled with nitrogen. If it is a liquid, the phenyl bromide is added under a stream of nitrogen using a syringe at ambient temperature, followed by DMEDA NN'dimethylethylene diamine (0.5 eq.) and degassed 1,4-dioxane (1.0 mL). The tube is sealed under positive nitrogen pressure, left under stirring and heated up to 110° C. After a reaction time of 6 h, the addition is made under stream of nitrogen of CsOH.H$_2$O (3 eq.) and 1 mL of degassed water. The tube is sealed under positive nitrogen pressure, left under stirring and heated up to 130° C. for 24 hours.

After cooling to ambient temperature, 10 mL of dichloromethane are added and 1 mL of HCl (37%). The mixture is stirred for two hours, 130 μL of 1,3-dimethoxybenzene (internal standard) are added. A small sample of reaction medium is taken and filtered through a Celite® pad, the solid is then washed with dichloromethane. The filtrate is analyzed by gas chromatography.

The filtrate is washed twice with water and the combined aqueous phases are extracted five times with dichloromethane. The organic phases are combined and dried over sodium sulfate, filtered and concentrated in vacuo to give the raw product which is purified by silica gel chromatography using a heptane and ethyl acetate mixture. The products are characterized by NMR. The yields with gas chromatography are determined with factor correction using authentic samples of the expected products.

Identification

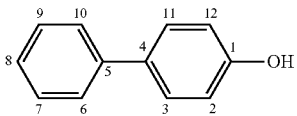

$^1$H NMR (400 MHz, CDCl$_3$):
δ 7.45-7.47 (m, 2H, H$_{6, 10}$), 7.39-7.42 (m, 2H, H$_{3, 11}$)) 7.31-7.36 (m, 2H, H$_{7,9}$), 7.21-7.24 (m, 1H, H$_8$), 6.83-6.85 (m, 2H, H$_{2, 12}$), 5.10 (1H, OH).
$^{13}$C NMR (100 MHz, CDCl$_3$): δ 155.24 (C$_1$), 140.83 (C$_5$), 134.00 (C$_4$), 128.76 (C$_{7, 9}$), 128.41 (C$_{3, 11}$), 126.71 (C$_{6, 10}$), 115.71 (C$_{2, 12}$).

TABLE 2

| Example No. | ArBr | ArOH | Yield [%] |
|---|---|---|---|
| 21 | Ph-Br | Ph-OH | 85, 75[a] |
| 22 | F-C$_6$H$_4$-Br | F-C$_6$H$_4$-OH | 70 |
| 23 | Ph-C$_6$H$_4$-Br | Ph-C$_6$H$_4$-OH | 90 |
| 24 | 2-bromonaphthalene | 2-naphthol | 88 |
| 25 | MeO-C$_6$H$_4$-Br | MeO-C$_6$H$_4$-OH | 87 |
| 26 | 3-MeO-C$_6$H$_4$-Br | 3-MeO-C$_6$H$_4$-OH | 85 |
| 27 | 4-Me-C$_6$H$_4$-Br | 4-Me-C$_6$H$_4$-OH | 80, 83[b] |

The yields were the isolated yields
[a]: 1,4-dioxane was substituted by DMSO
[b]: 1,4-dioxane was substituted by toluene

EXAMPLE 23

Biphenyl-4-ol

Following general operating mode B, 4-bromobiphenyl (232 mg, 1.0 mmol) was reacted with cesium hydroxide to give the expected product in the form of a brown solid with a yield of 90% (eluent: ethyl acetate/heptane 20:80).

GC/MS: rt=21.03 min, M/Z=170.
HRMS: 169.0649 (M−H). Theoretical: 169.0653.

EXAMPLE 24

2-naphthol

Following general operating mode B, 2-bromonaphthalene (207 mg, 1.0 mmol) was reacted with cesium hydroxide to give the expected product in the form of a white solid with a yield of 88% (eluent: ethyl acetat/heptane 20:80).

Identification

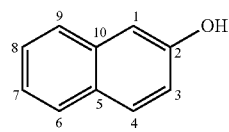

$^1$H NMR (400 MHz, CDCl$_3$): δ 7.65-7.69 (m, 2H, H$_{4,\,6}$), 7.60-7.58 (m, 1H, H$_9$), 7.32-7.36 (m, 1H, H$_8$), 7.22-7.26 (m, 1H, H$_7$), 7.05-7.06 (m, 1H, H$_1$), 7.00-7.03 (m, 1H, H$_3$), 5.06 (1H, OH).
$^{13}$C NMR (100 MHz, CDCl$_3$): δ 153.61 (C$_2$), 134.75 (C$_{10}$), 129.96 (C$_4$), 128.93 (C$_5$), 128.01 (C$_6$), 126.76 (C8), 126.41 (C9), 123.67 (C7), 117.73 (C3), 109.61 (C1).
GC/MS: rt=13.95 min, M/Z=144.
HRMS: 1430495 (M−H). Theoretical: 143.0497

EXAMPLE 26 m-methoxyphenol

Following general operating mode B, 3-methoxybromobenzene (127 µL, 1.0 mmol) was reacted with cesium hydroxide to give the expected product in the form of an oil with a yield of 85% (eluent: ethyl acetate/heptane 10:90).
Identification

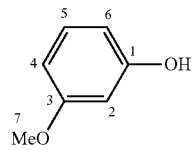

$^1$H NMR (400 MHz, CDCl$_3$): δ 7.03-7.08 (m, 1H, H$_5$), 6.41-643 (m, 1H, H$_4$), 6.34-6.36 (m, 2H, H$_{2,v6}$), 5.06 (1H, OH), 3.70 (s, 3H, H$_7$).
30.18 (C$_5$), 106.44 (C$_4$), 101.54 (C$_2$), 55.31 (C$_7$).
GC/MS: rt=11.63 min, M/Z=124.
HRMS: 123.0456 (M−H). Theoretical: 123.0446

EXAMPLE C

Influence of the Ligand

To test the extent of the hydroxylation reaction, various tests were performed starting from phenyliodide, causing the type of ligand to vary.

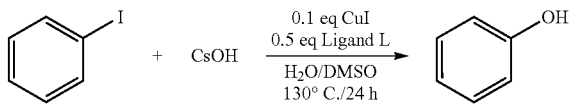 [SMILES: Ic1ccccc1 ; "CsOH" ; Oc1ccccc1]

Operating Mode of Example C:

After standard cycles of purging and filling with pure, dry nitrogen, a Radley tube (RR98030" Carrousel Reaction Station) or an oven-dried Schlenk tube, equipped with magnetic stir bar is charged with (0.1 eq.), CsOH.H$_2$O (3 eq.), iodophenyl if it is a solid (1 mmol, 1 eq.) and the ligand L (0.5 eq.) if it is a solid. The tube is then purged and re-filled with nitrogen. If it is a liquid the iodophenyl is added under a stream of nitrogen with a syringe at ambient temperature, and the ligand L (0.5 eq.) if it is a liquid is added with a syringe followed by degassed, anhydrous DMSO (1.0 mL) and 1 mL of degassed water. The tube is sealed under positive nitrogen pressure, stirred and heated to 130° C. for 24 hours. After cooling to ambient temperature, 10 mL of dichloromethane are added and 1 mL of (37%) HCl. The mixture is left under stirring for two hours, 130 µL of 1,3-dimethoxybenzene (internal standard) are added. A small sample of reaction mixture is taken and filtered through a Celite® pad, and the solid is washed with dichloromethane. The filtrate is then analyzed by gas phase chromatography.

The filtrate is washed twice with water. The aqueous phases are combined and extracted five times with dichloromethane. The organic phases are combined, dried over sodium sulfate, filtered and concentrated in vacuo to give the raw product.

The yields with gas phase chromatography are determined with factor correction using authentic samples of the expected products.

The results are given in Table 3.

TABLE 3

| Example N° | Ligands L | Yield (%) |
|---|---|---|
| L1 | di-tert-butyl-1,3-diketone | 95 |
| L2 | acetylacetone | 30 |
| L3 | dibenzoylmethane | 97 |
| L4 | N,N-dimethyl-acetoacetamide | ? |
| L5 | proline | 70 |
| L6 | 2'-hydroxyacetophenone | 85 |
| L7 | N,N'-dimethylethylenediamine | 84 |
| L8 | 1,10-phenanthroline | 75 |

The yield was determined using 1,3-dimethoxybenzene as standard.

Example D: synthesis of phenol and of diphenylether by hydroxylation of phenyliodide in the presence of a catalytic system comprising copper iodide and 1,3-ditertiobutyl-propane-1,3-dione Operating Mode of Example D:

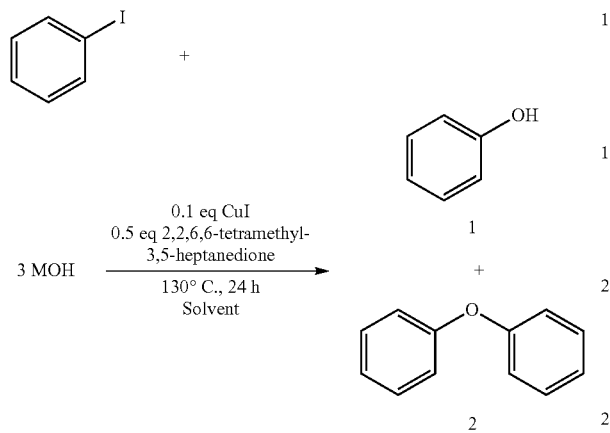

After standard cycles of purging and filling with pure, dry nitrogen, a Radley tube (RR98030" Carrousel Reaction Station) or an oven-dried Schlenk tube equipped with a magnetic stir bar is loaded with CuI (0.1 eq.), CsOH.H₂O (3 eq.), iodophenyl if it is a solid (1 mmol, 1 eq.). The tube is then purged and refilled with nitrogen. If it is a liquid, halogenophenyl is added under a stream of nitrogen using a syringe at ambient temperature and 2,2,6,6-tetramethyl-3,5-heptanedione (0.5 eq.), followed by anhydrous, degassed solvent (2.0 mL), if it is a co-solvent the total volume is 2 mL. The tube is sealed under positive nitrogen pressure, left under stirring and heated up to 130° for 24 hours. After cooling to ambient temperature, 10 mL of dichloromethane are added and 1 mL of HCl (37%).

The mixture is left under stirring for two hours, 130 μL of 1,3-dimethoxybenzene (internal standard) are added. A small sample of reaction mixture is taken and filtered through a Celite® pad, and the solid is washed with dichloromethane. The filtrate is then analyzed by gas chromatography.

The yields with gas phase chromatography are determined with factor correction using authentic samples of the expected products.

Example E: Various tests were conducted starting from phenyliodide, by causing the type of metal M and the type of solvent to vary.

The results are given in Table 4

TABLE 4

| Example N° | Solvent | MOH | Yield (%) 1 | 2 |
|---|---|---|---|---|
| S1 | NMP | KOH | 20 | 20 |
| S2 | H₂O | KOH | 20 | 0 |
| S3 | DMSO | KOH | 50 | 20 |
| S4 | DMSO/H₂O 7/1 | KOH | 19 | 28 |
| S5 | DMF/H₂O 7/1 | KOH | 15 | 20 |
| S6 | DMSO/H₂O 3/1 | KOH | 60 | 20 |
| S7 | DMF/H₂O 3/1 | KOH | 70 | 15 |
| S8 | DMSO/H₂O 3/1 | CsOH | 80 | 5 |
| S9 | MIBK/H₂O 3/1 | CsOH | 30 | 20 |

TABLE 4-continued

| Example N° | Solvent | MOH | Yield (%) 1 | 2 |
|---|---|---|---|---|
| S10 | NMP/H₂O 3/1 | CsOH | 30 | 20 |
| S11 | DMSO/H₂O 1/1 | CsOH | 95 | 0 |
| S12[b] | DMSO/H₂O 1/1 | CsOH | 45 | 0 |
| S13[c] | DMSO/H₂O 1/1 | CsOH | 40 | 25 |
| S14 | DMSO/H₂O 1/1 | KOH | 70 | 0 |

The yield was determined using 1,3-dimethoxybenzene as standard.

[b]: reaction conducted with 1.5 eq of CsOH
[c]: reaction conducted at 120° C.

The invention claimed is:

1. A method for producing hydroxylated halogenated aryl compounds, comprising conducting a hydroxylation reaction at a temperature lower than 200° C., wherein a compound having the formula:

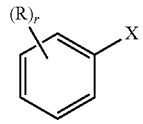

is reacted with MOH in the presence of a catalytic system comprising a copper-based catalyst and a ligand L to form a compound having the formula:

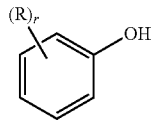

wherein:
R is selected from the group consisting of acceptor inductive effect groups and donor mesomer effect groups;
r is between 0 and 5;
X is a halogen atom;
M is selected from the group consisting of alkaline and alkaline-earth cations; and
L represents a compound of formula (I)

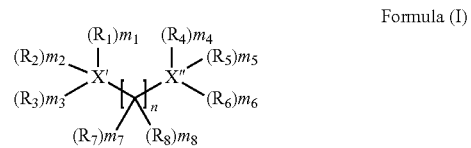

Formula (I)

wherein
X', X", the same or different, are selected from the group consisting of the nitrogen atom, the C=O group, the C=S group and the C—OH group;
$m_1$ to $m_8$, the same or different, represent 0 or 1;
n represents 1 or 2;
$R_1, R_2, R_3, R_4, R_5, R_6, R_7$ and $R_8$, the same or different, are selected from the group consisting of:
a hydrogen atom;
a branched, linear, monocyclic or polycyclic hydrocarbon group comprising 1 to 20 carbon atoms and optionally comprising one or more unsaturations in the form of double and/or triple bond(s);

a primary, secondary or tertiary —NR'R" amine, wherein R' and R", the same or different, represent a $C_1$ to $C_{10}$ alkyl group; a hydroxyl group;

or $R_4$, X" and $R_7$ form a heterocyclic group;

or $R_1$, X' and $R_7$ form a phenol group;

or $R_1$, X', X", $R_7$ and $R_4$ form a polycyclic group formed of at least 3 saturated and/or unsaturated rings, or of at least 3 rings of which only one or two thereof is (are) aromatic and forming between them, ortho- or ortho- and peri-condensed systems.

2. The method according to claim 1, wherein in formula (I):

$R_1$, $R_2$, $R_3$, $R_4$, $R_5$, $R_6$, $R_7$ and $R_8$, the same or different, represent:

a hydrogen atom;

a $C_1$ to $C_{10}$ alkyl group;

an aryl group; or a primary, secondary or tertiary —NR'R" amine wherein R' and R", the same or different, represent a hydrogen atom, a $C_1$ to $C_{10}$ alkyl group, a hydroxyl group;

$R_7$ and $R_8$, the same or different, represent a hydrogen atom; or $R_4$, X" and $R_7$ form a heterocyclic group; or $R_1$, X' and $R_7$ form a phenol group; or $R_1$, X', X", $R_7$ and $R_4$ form a polycyclic group formed of a least 3 saturated and/or unsaturated rings, or of at least 3 rings of which only one or two thereof are aromatic and forming between them ortho- or ortho- and peri-condensed systems.

3. The method according to claim 1 wherein in formula (I):

X', X", the same or different and are selected from the group consisting of the nitrogen atom, the C=O group, the C=S group and the C—OH group;

n represents 1;

$m_4$, $m_7$ and $m_8$ represent 1; $m_1$, $m_2$, $m_3$, $m_5$ and $m_6$ represent 0 or 1;

$R_1$, $R_2$, $R_3$, $R_5$, $R_6$ the same or different are selected from the group consisting of:

a hydrogen atom;

a branched, linear or cyclic (mono- or polycyclic) hydrocarbon group comprising 1 to 20 carbon atoms, and possibly comprising one or more unsaturations in the form of double and/or triple bond(s);

a primary, secondary or tertiary —NR'R" amine, wherein R' and R" the same or different represent a $C_1$ to $C_{10}$ alkyl group; and a hydroxyl group;

$R_8$ represents H and $R_4$, X" and $R_7$ form a heterocyclic group; or

X', X", the same or different, are selected from the group consisting of the nitrogen atom, the C=O group, the C=S group and the C—OH group;

n represents 1;

$m_2$ to $m_6$ represent 0 or 1; $m_1$, $m_7$ and $m_8$ represent 1;

$R_1$ to $R_6$, the same or different, are selected from the group consisting of:

a hydrogen atom;

a branched, linear or cyclic (mono- or polycyclic) hydrocarbon group comprising 1 to 20 carbon atoms and possibly comprising one or more unsaturations in the form of double and/or triple bond(s);

a primary, secondary or tertiary —NR'R" amine, wherein R' and R" the same or different represent a $C_1$ to $C_{10}$ alkyl group, preferably $C_1$ to $C_6$, linear or branched, preferably methyl; and a hydroxyl group;

$R_1$, X' and $R_7$ form a phenol group and $R_8$ represents H; or

X', X", the same or different, are selected from the group consisting of the nitrogen atom, the C=O group, the C=S group and the C—OH group;

n represents 2;

$m_2$, $m_3$ $m_5$, $m_6$ and $m_8$ represent 0 or 1; $m_1$, $m_4$ and $m_7$ represent 1;

$R_2$, $R_3$, $R_5$, $R_6$ and $R_8$, the same or different, are selected from the group consisting of:

a hydrogen atom;

a branched, linear or cyclic (mono- or polycyclic) hydrocarbon group comprising 1 to 20 carbon atoms and possibly comprising one or more unsaturations in the form of double and/or triple bond(s);

a primary, secondary or tertiary —NR'R" amine, wherein R' and R" the same or different represent a $C_1$ to $C_{10}$ alkyl group; and a hydroxyl group;

$R_1$, X', X", $R_7$ and $R_4$ form a polycyclic group comprising at least 3 saturated and/or unsaturated rings, or at least 3 rings of which one thereof or two thereof are aromatic and form between them ortho- or ortho- and peri-condensed systems.

4. The method according to claim 1 wherein L is selected from the group consisting of:

5. The method according to claim 1 conducted at a temperature lower than 150° C.

6. The method according to claim 1 wherein X is selected from in the list consisting of bromine or iodine.

7. The method according to claim 1 wherein X is iodine.

8. The method according to claim 1 wherein X is bromine.

9. The method according to claim 8 wherein R is an acceptor inductive effect group.

10. The method according to claim 1 wherein R is an acceptor inductive effect group selected in the list consisting of the $NO_2$ group, the $CO_2Me$ group, the CN group, a halogen atom and the methoxy group.

11. The method according to claim 1 wherein R is a donor mesomer effect group selected in the list consisting of phenyl, a hydroxyl group, a methyl group, the fluorine atom, the hydrogen atom and a methoxy group or R together with the phenyl forms a naphthyl group.

12. The method according to claim 1 wherein the cation M is selected in the list consisting of the salts of potassium or cesium.

13. The method according to claim 1 wherein the hydroxylation reaction is conducted in two steps, wherein a compound having the formula:

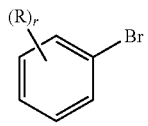

is reacted with MOH in the presence of a catalytic system comprising a copper-based catalyst and a ligand L and a metallic iodide to form a compound having the formula:

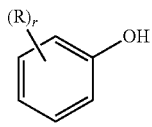

and wherein:
the first step corresponds to a nucleophilic substitution of bromobenzene by a metallic iodide in the presence of a copper-based catalyst and a ligand, and
the second step corresponds to the hydroxylation reaction in the presence of a copper-based catalyst and a ligand.

14. The method according to claim 13 wherein the metallic iodide is selected from the group consisting of NaI, KI and CsI.

15. The method according to claim 13 wherein the molar ratio between the number of moles of metallic iodide and the number of moles of brominated compound varies between 0.1 and 4.

16. The method according to claim 13 wherein the copper-based catalysts are selected in the list consisting of metallic coppers, copper (I) or copper (II) oxides, copper (I) or copper (II) hydroxides, the inorganic or organic salts of copper (I) or copper (II), and the complexes of copper (I) or copper (II) with usual ligands.

17. The method according to claim 16 wherein the copper-based catalysts are selected in the group consisting of copper (0), copper halides, copper oxides or hydroxides, copper nitrates, copper sulfates or sulfites, the organic salts of copper wherein the counter-ion has at least one carbon atom.

18. The method according to claim 1 wherein for which the molar ratio between the number of moles of copper-based catalyst and the number of moles of halogenated aryl compound is comprised between 0.001 and 0.5.

19. The method according to claim 1 wherein the molar ratio between the number of moles of ligand L and the number of moles of halogenated aryl compound varies between 0.001 and 0.9.

20. The method according to claim 1 wherein the molar ratio between the number of moles of MOH and the number of moles of brominated aryl compound varies between 0.1 and 5.

21. The method according to claim 1 wherein the branched, linear, monocyclic or polycyclic hydrocarbon group is methyl, isobutyl or phenyl.

22. The method according to claim 1 wherein R' and R'', the same or different, represent a $C_1$ to $C_6$ alkyl group.

23. The method according to claim 15 wherein the number of moles of brominated compound varies between 1 and 3.

* * * * *